United States Patent [19]
Kirsch

[11] Patent Number: 5,741,257
[45] Date of Patent: Apr. 21, 1998

[54] MEMBRANE FOR TEMPORARILY COVERING A BONE SURGERY SITE

[76] Inventor: Axel Kirsch, Talstrasse 23, D70794 Filderstadt, Germany

[21] Appl. No.: 493,588

[22] Filed: Jun. 22, 1995

Related U.S. Application Data

[62] Division of Ser. No. 188,584, Jan. 28, 1994, abandoned.

[51] Int. Cl.⁶ ..................................................... A61B 17/56
[52] U.S. Cl. ................... 606/69; 606/77; 606/86; 606/215
[58] Field of Search .................... 606/53, 60, 69, 606/70, 72, 77, 76, 86, 213, 215

[56] References Cited

U.S. PATENT DOCUMENTS

| | | |
|---|---|---|
| 4,365,357 | 12/1982 | Draenert . |
| 4,429,691 | 2/1984 | Niwa et al. ............................... 606/77 |
| 4,539,981 | 9/1985 | Tune . |
| 5,013,315 | 5/1991 | Barrows ...................................... 606/71 |
| 5,084,051 | 1/1992 | Tormala et al. ........................... 606/77 |
| 5,196,016 | 3/1993 | Buser et al. . |
| 5,275,602 | 1/1994 | Shimizu et al. ............................ 606/72 |
| 5,346,492 | 9/1994 | Morgan . |
| 5,380,328 | 1/1995 | Morgan . |

FOREIGN PATENT DOCUMENTS

| | | |
|---|---|---|
| 0 189 546 | 8/1986 | European Pat. Off. . |
| 0 190 422 | 8/1986 | European Pat. Off. . |
| 38 31 657 A1 | 3/1990 | Germany . |
| PS 39 01 811 C1 | 4/1990 | Germany . |
| 91 15 341 U | 4/1992 | Germany . |
| 197 711 | 11/1977 | U.S.S.R. . |
| 2 056 882 | 3/1981 | United Kingdom . |
| 2 142 544 | 1/1985 | United Kingdom . |
| WO 87/00419 | 1/1987 | WIPO . |

*Primary Examiner*—Guy V. Tucker
*Attorney, Agent, or Firm*—Hill, Steadman & Simpson

[57] ABSTRACT

A membrane for temporarily covering a recess in the endogenic bone tissue filled with an osteogenic material, such as hydroxyapatite granules, as is needed following reconstruction of bones in plastic surgery or operations on the jaw, is composed of resorbable membrane material.

21 Claims, 2 Drawing Sheets

MEMBRANE FOR TEMPORARILY COVERING A BONE SURGERY SITE

This is a divison of application Ser. No. 08/188,584, filed Jan. 28, 1994, now abandoned.

FIELD OF THE INVENTION

The present invention relates to membranes of the type employed for the temporarily covering a recess in the endogenic bone tissue filled with an osteogenic material, such as hydroxyapatite granules.

DESCRIPTION OF THE PRIOR ART

Following bone surgery, for example, in the reconstruction of bones in plastic surgery or in the case of operations on the jaw, it is standard practice to fill the bone defect or deficiency points, which are in the form of recesses or cavities in the endogenic bone tissue, with an osteogenic material. Such osteogenic material generally consists of a mixture of bone replacement material, such as hydroxyapatite granules and endogenic bone particles. To ensure that the osteogenic material grows substantially exclusively in an osseous manner from the bone side, but does not grow into surrounding mucous tissue, the recess is closed with a covering membrane of the type generally described above. The purpose of such a membrane is to ensure that there is no growth of the osteogenic material into the non-bone tissue. Only by ensuring complete osseous growth of the osteogenic material is it possible to substantially completely eliminate the bone defect point, and to reintegrate the osteogenic material into the endogenic bone after osseous growth has taken place.

Heretofore, polytetrafluoroethylene films have been used as such covering membranes, however, such known membranes have the disadvantage of remaining in the body when the bone defect point heals, and can therefore create complications.

SUMMARY OF THE INVENTION

It is an object of the present invention to provide a membrane for temporarily covering a recess in endogenic bone tissue filled with an osteogenic material which avoids complications subsequent to the healing of the bone defect points.

The above object is achieved in accordance with the principles of the present invention in a covering membrane of the type generally described above which is made from absorbable or resorbable membrane material. Such membrane material is more rapidly resorbable from the side remote from the endogenic bone than from the side facing the endogenic bone.

In a further embodiment of the invention, the membrane material consists of material having a density which increases from the side remote from the endogenic bone to the side facing the endogenic bone.

In a further embodiment of the invention, the membrane may be formed by several layers having different densities and/or compositions.

The membrane material may include several woven or knitted layers of different textures.

The membrane material may at least partially consist of lyophilized dura mater.

The membrane material may consist at least partly of polylactide/vicryl. The membrane material may also at least partially consist of collagen.

The membrane material may also at least partly consist of polylactide.

The membrane material may also partly consist of oxymethyl cellulose.

The covering membrane of the invention may exhibit a resorbability gradient which decreases from the side of the membrane remote from the endogenic bone to the side of the membrane facing the endogenic bone, such that the membrane material layer in direct contact with the bone is only resorbed by the endogenic tissue if the recess of the endogenic bone closed by the membrane has substantially ossified and become reintegrated into the bone.

The membrane may be augmented by a stiffening layer in the form of a perforated metal plate or the like, the metal plate may consist of titanium.

The disadvantages of known covering membranes, which are not degradable or resorbable into the body are avoided by using a membrane material in accordance with the principles of the present invention which is resorbable in the body. Preferably a membrane material is employed which exhibits a resorbability decreasing from a side of the membrane remote from the endogenic bone tissue to the side of the membrane facing the endogenic bone tissue. As a result, the covering membrane is substantially completely resorbed from the side remote from the bone, so that the osseous growth of the osteogenic material, and therefore the healing of the bone defect, can occur substantially undisturbed by inflammation which may accompany any resorption of exogenic tissue.

If the covering membrane is provided with stiffening layer, which can be disposed on the side of the covering membrane facing or remote from the bone, or separately from the membrane, it is possible to prevent any impairment of the osteosynthesis process by movement of the covering membrane, so that the overall osteogenic process is assisted.

DESCRIPTION OF THE PREFERRED EMBODIMENTS

Figure 1:
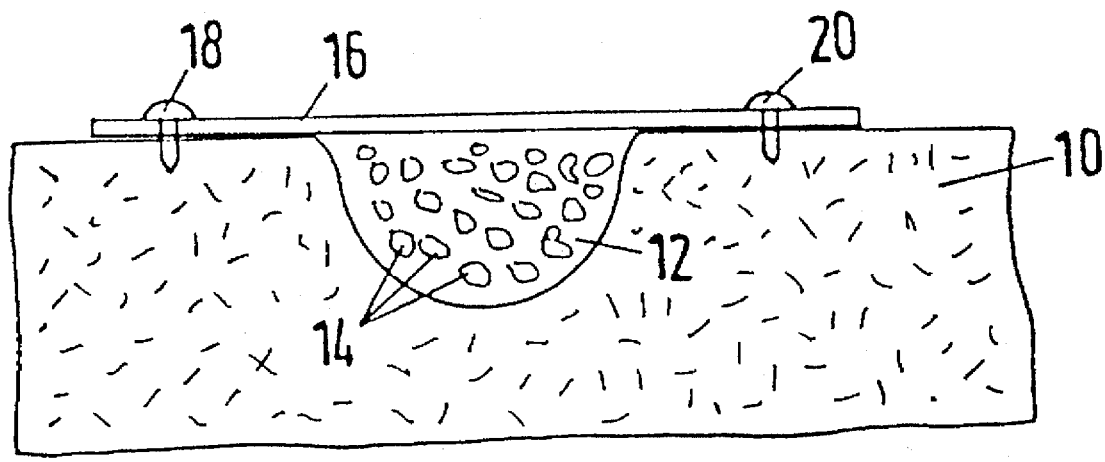
FIG. 1 is schematic illustration of a bone defect point covered by a membrane constructed in accordance with the principles of the present invention, shown in section at a right angle to the membrane plane.

As shown in FIG. 1, a bone defect point is formed by a recess 12 in an endogenic bone 10, and is substantially completely filled with osteogenic material 14. The osteogenic material 14 may be constituted by hydroxyapatite granules which are mixed in known manner with bone particles comprising endogenic bone tissue. The recess 12 filled with the osteogenic material 14 is covered by a covering membrane 16 constructed in accordance with the principles of the present invention, which is tightly engaged on the endogenic bone 10 completely surrounding the recess 12 by means of fixing pins 18 and 20. The function of the covering membrane 16 is to ensure the osseous growthrough of the osteogenic material 14 from the endogenic bone 10 in such a way that any growth of the osteogenic material with anything other than bone tissue and in particular with mucous tissue is prevented.

Figure 2:
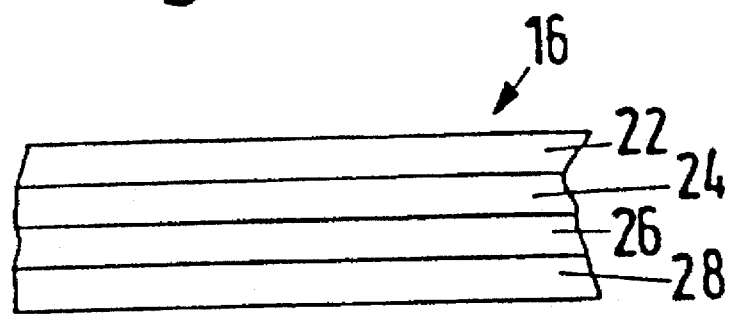
FIG. 2 shows the covering membrane of FIG. 1 in a section at a right angle to the membrane plane, significantly enlarged.

In the embodiment shown in FIG. 2, the covering membrane 16 is formed by several layers 22, 24, 26 and 28, the density of these layers increasing from a side (represented by layer 22) remote from the bone 10 in the applied state (FIG. 1) to the side (represented by layer 28) of the membrane facing the bone. This can be accomplished in the representative embodiment by forming all of the layers 22 through 28 from collagen tissue, i.e., all of the layers in this embodiment have the same composition, but the weave in the layer 22 is relatively open, whereas the weave in the layer 28 is close, with the intervening layers having weaves of intermediate openness to achieve the desired density gradient. (The density and/or resorbability gradients can alternatively be achieved by layers of respectively different compositions, or differences in a combination of weaves and compositions can be employed to achieve such gradients.)

As a result of the increasing density of the covering membrane 16 from the layer 22 to the layer 28, it is ensured that the covering membrane 16 is resorbed from the side thereof remote from the bone, i.e., the layer 28 facing the bone 10 is resorbed last, after the recess 12, or the osteogenic material 14 located therein, has been substantially ossified with endogenic bone mass, and has therefore become integrated into the bone 10.

Figure 3:
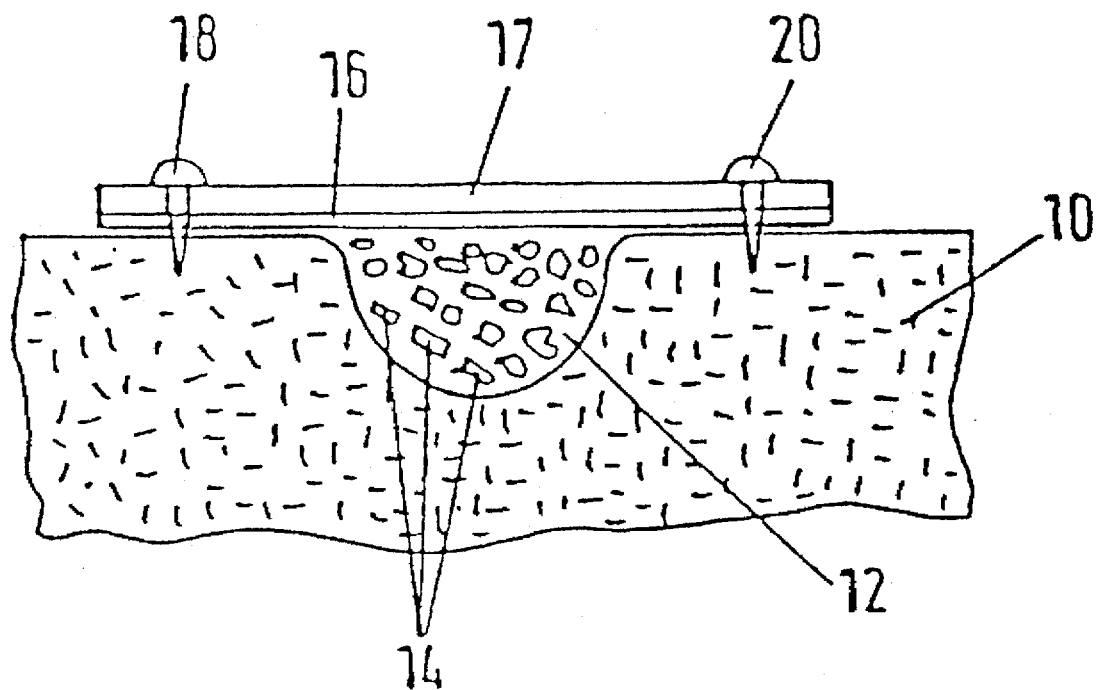
FIG. 3 is a schematic illustration of a bone defect point covered by the inventive membrane, augmented with a stiffening plate.
Figure 4:
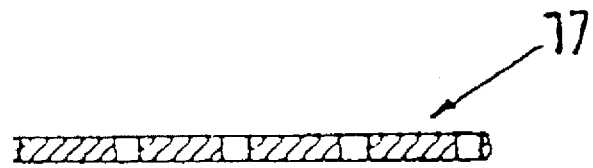
FIG. 4 is a sectional view (enlarged) of an embodiment of the stiffening plate of FIG. 3.

The membrane may be augmented, as shown in FIG. 3, with a stiffening plate 17 in the form of a metal plate or the like. The plate 17 may be a titanium plate, and may be perforated as shown in FIG. 4.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for promoting bone knitting at a bone recess in endogenic bone tissue comprising:

filling a recess in endogenic bone tissue with an osteogenic material;

covering the recess filled with the osteogenic material with a membrane consisting of a plurality of layers of woven membrane material with respectively different weave openness and said membrane having a resorbability gradient from a first side of said membrane to a second side of said membrane with said resorbability gradient decreasing from a highest resorbability at said first side to a lowest resorbability at said second side; and temporarily attaching said membrane over said recess with said second side of said membrane facing said endogenic bone to cause said membrane material to be more rapidly resorbed from said first side than from said second side.

2. A method as claimed in claim 1 comprising the step of selecting material including lyophilized dura mater as said resorbable material for said membrane.

3. A method as claimed in claim 1 comprising the step of selecting material including collagen as said resorbable material for said membrane.

4. A method as claimed in claim 1 comprising the step of selecting material including polylactide as said resorbable material for said membrane.

5. A method as claimed in claim 1 comprising the step of selecting material including oxymethyl cellulose as said resorbable material for said membrane.

6. A method as claimed in claim 1 wherein the step of covering the recess with a membrane comprises covering said recess with a membrane having a stiffening layer formed by a perforated plate.

7. A method as claimed in claim 6 comprising selecting a plate consisting of metal as said perforated plate.

8. A method as claimed in claim 7 comprising selecting a plate consisting of titanium.

9. A method for promoting bone knitting at a bone recess in endogenic bone tissue comprising:

filling a recess in endogenic bone tissue with an osteogenic material;

covering the recess filled with the osteogenic material with a membrane consisting of membrane material and a stiffening layer formed by a perforated plate, and having a resorbability gradient from a first side of said membrane to a second side of said membrane with said resorbability gradient decreasing from a highest resorbability at said first side to a lowest resorbability at said second side; and temporarily attaching said membrane over said recess with said second side of said membrane facing said endogenic bone to cause said membrane material to be more rapidly resorbed from said first side than from said second side.

10. A method as claimed in claim 9 wherein the step of covering the recess with a membrane comprises covering said recess with a membrane consisting of a plurality of layers having respectively different compositions.

11. A method as claimed in claim 9 wherein the step of covering the recess with a membrane comprises covering said recess with a membrane consisting of a plurality of layers having respectively different densities.

12. A method as claimed in claim 9 wherein said resorbability gradient comprises a density gradient having a lowest density at said first side of said membrane remote from said endogenic bone and a highest density at a second side of said membrane facing said endogenic bone.

13. A method as claimed in claim 12 wherein the step of covering the recess with a membrane comprises covering said recess with a membrane consisting of a plurality of layers having respectively different compositions.

14. A method as claimed in claim 12 wherein the step of covering the recess with a membrane comprises covering said recess with a membrane consisting of a plurality of layers having respectively different densities.

15. A method as claimed in claim 14 wherein the step of covering the recess with a membrane comprises covering said recess with a membrane having layers consisting of woven material with respectively different weave openness.

16. A method as claimed in claim 9 comprising the step of selecting material including lyophilized dura mater as said resorbable material for said membrane.

17. A method as claimed in claim 9 comprising the step of selecting material including collagen as said resorbable material for said membrane.

18. A method as claimed in claim 9 comprising the step of selecting material including polylactide as said resorbable material for said membrane.

19. A method as claimed in claim 9 comprising the step of selecting material including oxymethyl cellulose as said resorbable material for said membrane.

20. A method as claimed in claim 9 comprising selecting a plate consisting of metal as said perforated plate.

21. A method as claimed in claim 20 comprising selecting a plate consisting of titanium.

* * * * *